United States Patent [19]
Goble et al.

[11] Patent Number: 5,549,613
[45] Date of Patent: Aug. 27, 1996

[54] MODULAR SURGICAL DRILL

[75] Inventors: E. Marlowe Goble; David P. Luman, both of Logan, Utah; Harold M. Martins, Newton, Mass.

[73] Assignee: Mitek Surgical Products, Inc., Westwood, Mass.

[21] Appl. No.: 122,202

[22] Filed: Sep. 15, 1993

[51] Int. Cl.⁶ .................................................. A61B 17/56
[52] U.S. Cl. ........................... 606/80; 606/180; 408/231; 408/713
[58] Field of Search .................................. 606/80, 81, 79, 606/84, 85, 86, 88, 96, 98, 102, 180; 433/165; 408/203.5, 204, 226, 227, 229, 231, 232, 233, 713, 57, 59

[56] References Cited

U.S. PATENT DOCUMENTS

| | | | |
|---|---|---|---|
| 3,554,192 | 1/1971 | Isberner | 606/80 X |
| 3,667,456 | 6/1972 | Charnley | 606/81 X |
| 3,687,565 | 8/1972 | Byers et al. | 408/201 |
| 5,190,548 | 3/1993 | Davis | 606/80 |
| 5,197,967 | 3/1993 | Wilson | 606/79 |
| 5,341,816 | 8/1994 | Allen | 128/754 |
| 5,374,269 | 12/1994 | Rosenberg | 606/80 |

FOREIGN PATENT DOCUMENTS 253526  1/1988  European Pat. Off. ................. 606/80

Primary Examiner—Guy Tucker
Attorney, Agent, or Firm—Pandiscio & Pandiscio

[57] ABSTRACT

A modular surgical drill in the form of a rigid drill shaft and a drill bit which are connected together at the rear end of the drill bit and the forward end of the drill shaft by a tongue-and-groove arrangement. Each of the shaft and drill bit are provided with through bores extending centrally through their entire length. These bores become aligned upon assembly of the drill bit and shaft. The modular drill is intended to be employed with a guidewire for drilling holes into bone. The assembled drill bit and shaft are placed on the guidewire and moved down such guidewire into contact with the bone, whereupon a tunnel may be formed into the bone by rotating and advancing the drill bit along the guidewire. The dimensions of the bore and guidewire are so selected as to prevent the drill bit and drill shaft from moving relative to one another once they are assembled and mounted upon the guidewire.

13 Claims, 19 Drawing Sheets

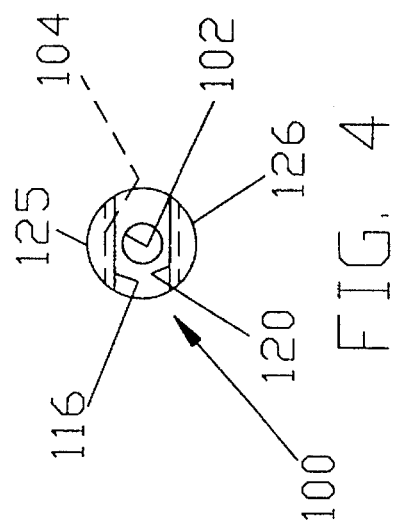
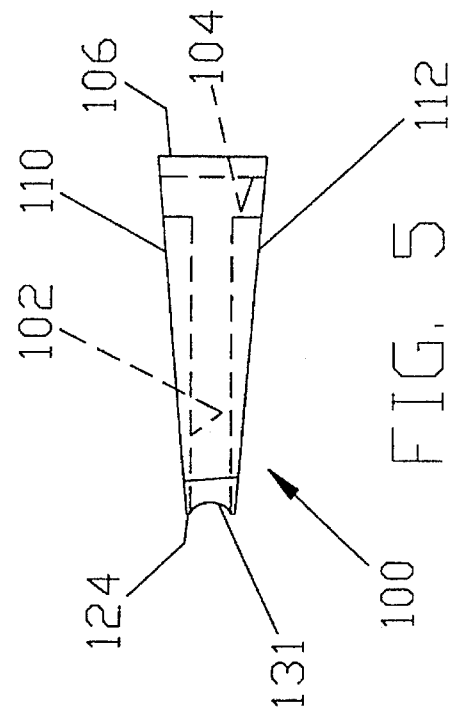
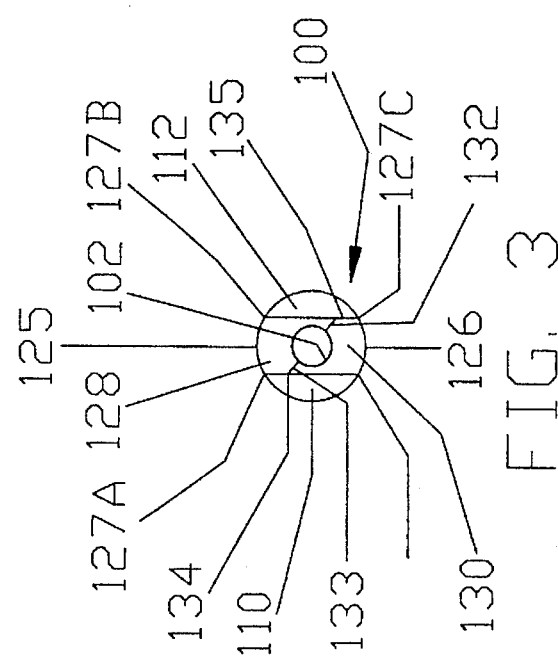

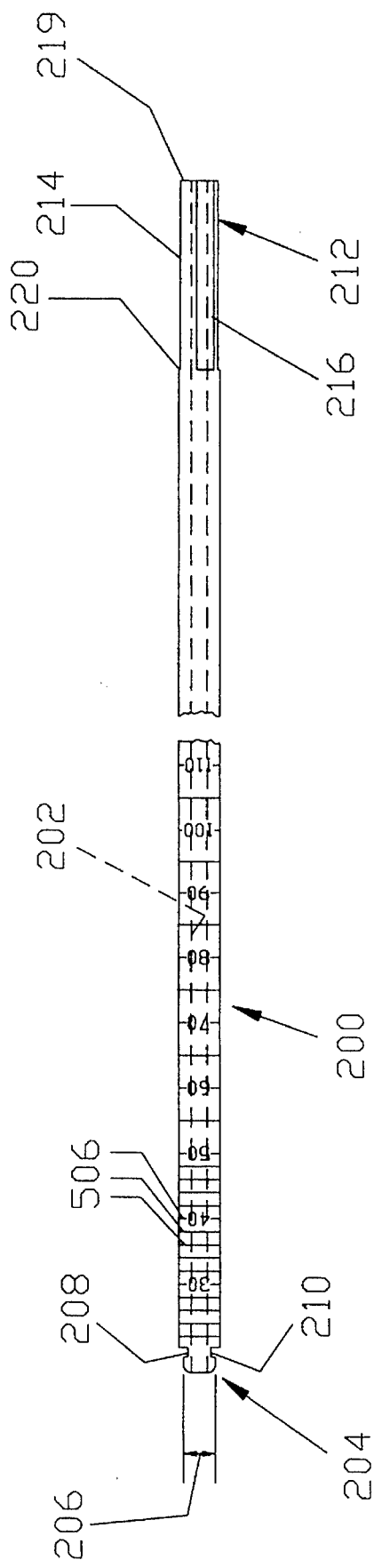
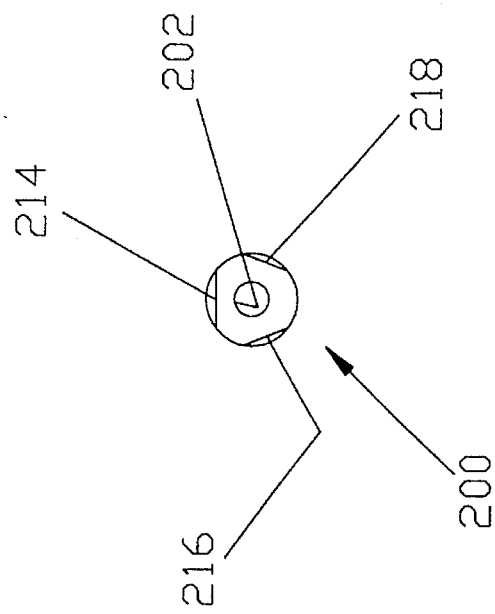
FIG. 6
FIG. 7
FIG. 8

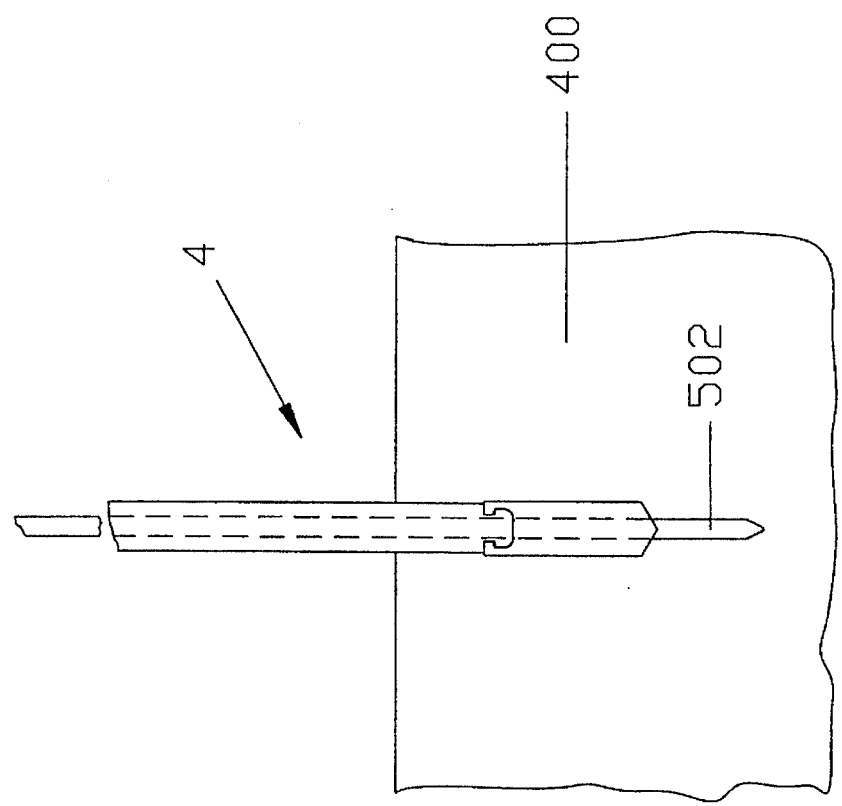
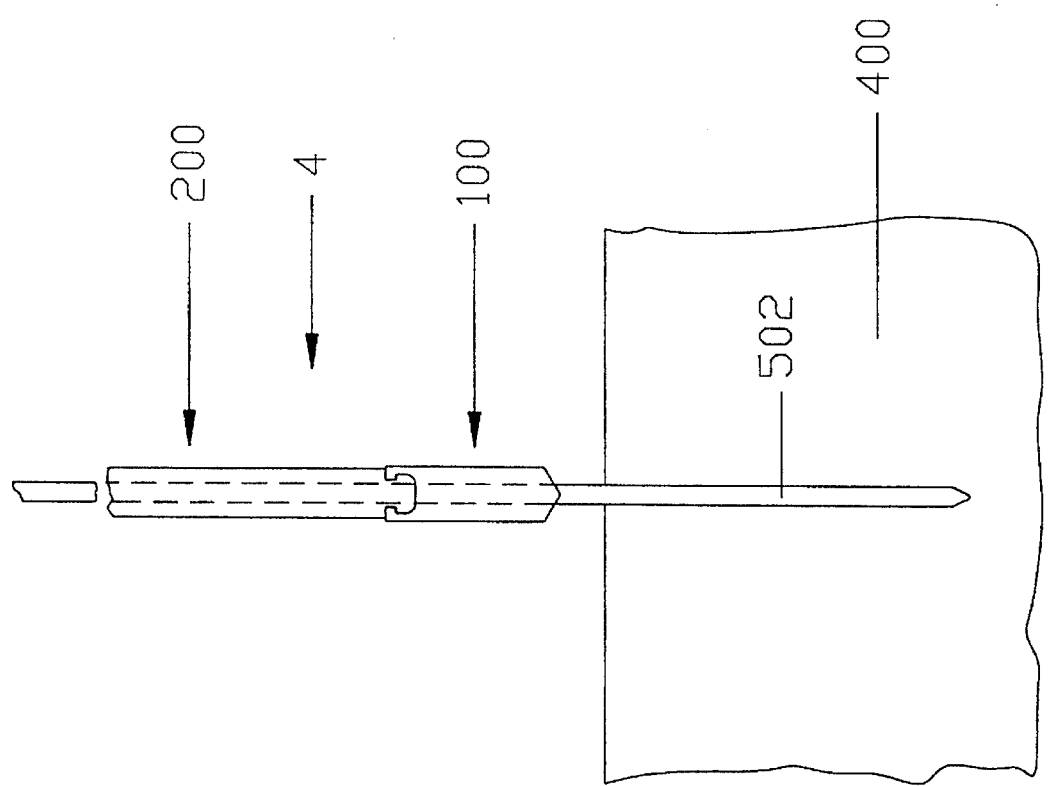

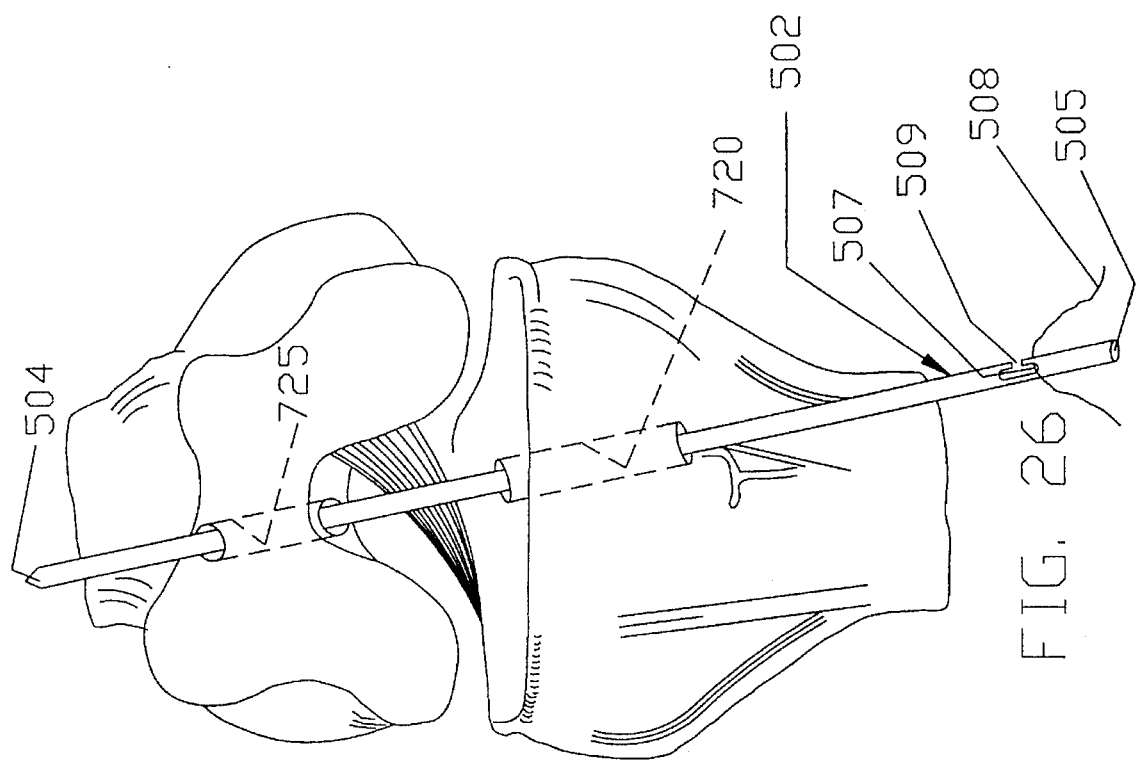

MODULAR SURGICAL DRILL

FIELD OF THE INVENTION

The present invention relates to drilling implements for use in carrying out surgical procedures, and is more particularly concerned with a drill bit and shaft assembly which forms part of a surgical drilling implement.

BACKGROUND OF THE INVENTION

In carrying out certain surgical procedures, it is often necessary to form holes into or through bones. In some situations it may be necessary to form multiple holes having different diameters. It may also be necessary to form a hole in a bone on the first pass of a surgical drill of one diameter, and then to widen that hole (along either part of or all of its length) on a successive pass of a second, larger diameter drill.

To accomplish drilling into bone, one method that has been employed involves first placing a thin guidewire into a bone. Such a guidewire is frequently made of stainless steel. It is typically placed into the bone by tapping on the proximal end of the guidewire or by drilling. After the guidewire is thus installed, it is used to direct one or more drills down its length to effect a drilling operation. For example, the diameter of a tunnel that is formed into the bone using a first drill passed down a guidewire may be sequentially increased (along either part of or all of its length) by employing drills of increasingly larger size and passing them successively down the guidewire into drilling engagement with the bone.

Unfortunately, it can be time-consuming and inconvenient to successively chuck and remove multiple drill bits from a surgical drill during the course of a surgical procedure.

Accordingly, one object of the present invention is to provide a modular drill arrangement in which different drill bits may be readily interchanged on a rigid drill shaft in order to form different sized holes in bone.

Another object of the present invention is to provide a modular drill implement wherein a drill shaft need be chucked only once in a surgical drill in order to complete a surgical procedure which requires making different sized holes in bone.

A further object of the present invention is to provide a method of constructing tunnels in bone wherein a modular drill having a drill bit and a rigid drill shaft is employed in connection with a guidewire, and the interconnection of the drill bit and the rigid drill shaft is secured against displacement by the mounting of the modular drill on the guidewire.

Yet another object of the present invention is to provide a modular drill for use with a guidewire for drilling holes into bone wherein alignment of the drill bit is assured when drilling into bone even though the drill bit may be replaced with another drill bit during the surgical procedure.

A still further object of the present invention is to provide a surgical drilling implement which employs a drill bit and drill shaft, and wherein the interconnection between the drill bit and shaft is such as to readily permit interchanging drill bits, and wherein such drill bits are securely locked relative to the shaft.

Another object of the present invention is to provide a drill bit which, when drilled through bone and upon entering a joint capsule, will not damage adjacent soft tissue structures.

Yet another object of the present invention is to provide means for retrieving a drill bit which becomes disengaged from its associated drill shaft during use.

Still another object of the present invention is to provide improved means for mounting a drill bit to a drill shaft.

And another object of the present invention is to provide a modular drill which will avoid migrating off its drilling axis as it exits the far side of a bone even when that drilling axis extends at an acute angle to the rear surface of the bone.

Yet another object is to provide improved means for forming a bone tunnel through a bone, and thereafter passing a length of suture through that bone tunnel.

SUMMARY OF THE INVENTION

These and other objects of the present invention are achieved by providing a novel modular drill which employs a tongue and groove arrangement between one end of a drill bit and a mating end of a rigid drill shaft to effect attachment of one to the other. In addition, both the drill bit and the rigid drill shaft are formed with a through hole for mounting upon a guidewire after they are assembled to one another. A close fit is provided between the guidewire and the modular drill so as to prevent the drill bit and shaft from moving relative to one another once the preassembled drill has been mounted on the guidewire.

The method of employing such a modular drill contemplates that after the placement of a guidewire in a bone by means of drilling or tapping, a preassembled drill bit and shaft are placed onto the guidewire and passed down the guidewire into contact with the bone, whereupon the drill bit is advanced into the bone to a desired depth, or completely through the bone, to create a tunnel in the bone. Thereafter, the modular drill is removed from the guidewire. When desired, a modular drill bit of a different size may be mounted on the same drill shaft without removing the drill shaft from the chuck. If desired, drill bits of successively larger diameter may be mounted on the shaft and passed down the same guidewire so as to progressively enlarge the diameter of the tunnel thus created. The sizing of the through hole through the drill bit and the drill shaft relative to the diameter of the guidewire is such as to create a close sliding fit, thereby assuring that the drill bit and shaft cannot move relative to one another once the drill bit and drill shaft are mounted on the guidewire. Also, the fit between the guidewire and modular drill is such as to permit relative rotation therebetween.

BRIEF DESCRIPTION OF THE DRAWINGS

These and other objects and features of the present invention are more fully disclosed or rendered obvious by the following detailed description of the invention, which is to be considered together with the accompanying drawings wherein like numbers refer to like parts, and further wherein:

FIG. 3 is a front view of the drill bit of the present invention that is shown in FIG. 2;

FIG. 4 is a rear view of the drill bit of the present invention that is shown in FIG. 2;

FIG. 5 is a top view of the drill bit of the present invention that is shown in FIG. 2;

FIG. 6 is an enlarged side view of the rigid drill shaft shown in FIG. 1;

FIG. 7 is a front end view of the rigid drill shaft of the present invention that is shown in FIG. 6;

FIG. 8 is a rear end view of the rigid drill shaft of the present invention that is shown in FIG. 6;

FIG. 11 is a side view of the same piece of bone, with an assembled modular drill being introduced onto the guidewire;

FIG. 12 is a side view of the same piece of bone, with the modular drill shown in FIG. 11 being advanced to cut into the bone to create a tunnel;

FIG. 26 shows a guide wire with suture pulling means for passing a suture through a bone tunnel.

DETAILED DESCRIPTION OF THE INVENTION

A preferred embodiment of the modular drill bit and rigid drill shaft of the present invention is shown in FIGS. 1 through 8, inclusive.

Figure 1:
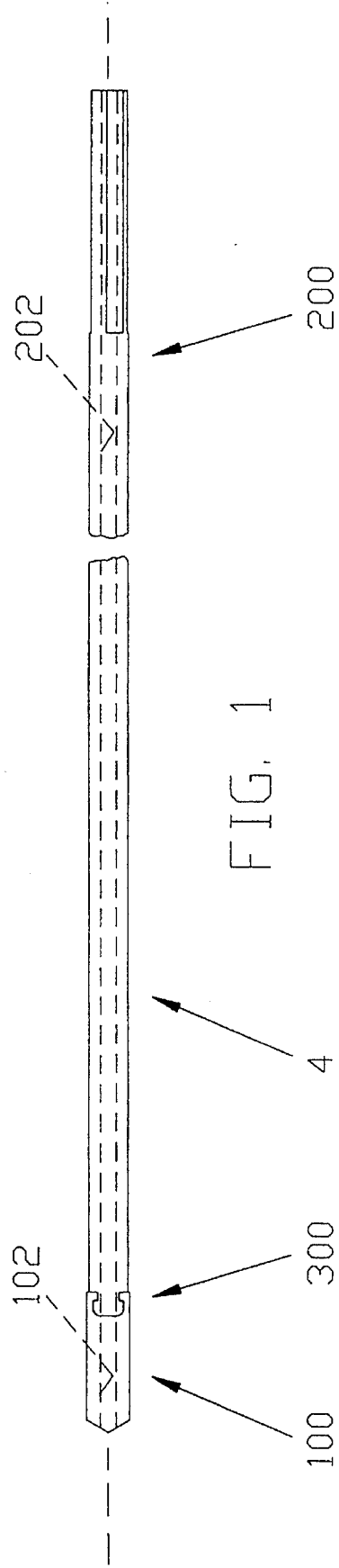
FIG. 1 is a side view illustrating a preferred form of the modular drill of the present invention and showing an assembled drill bit and rigid drill shaft.

Looking first at FIG. 1, there is shown a modular drill 4 which comprises two parts that are assembled together, i.e., a drill bit 100 and a rigid drill shaft 200. In this preferred embodiment these two members are assembled together by means of a tongue-and-groove interconnection 300. A bore 102 extends the full length of the drill bit 100, and a bore 202 extends the full length of the shaft 200. Bore 202 may have a constant diameter along its length, in which case the diameter of bore 202 is substantially the same as the diameter of bore 102 (see FIGS. 1 and 6). Alternatively, bore 202 may have two or more different diameters along its length, in which case the smallest of these diameters is substantially the same as the diameter of bore 102 and the remaining diameters are somewhat larger in size (see FIG. 6A). This latter arrangement is preferred in some cases so as to minimize any binding of the rigid shaft 200 on the guidewire during drilling. Regardless of whether bore 202 is formed with a single diameter or multiple diameters, the two bores 102 and 202 are in alignment when the drill bit 100 is interconnected to the drill shaft 200 as shown in FIG. 1.

Figure 2A:
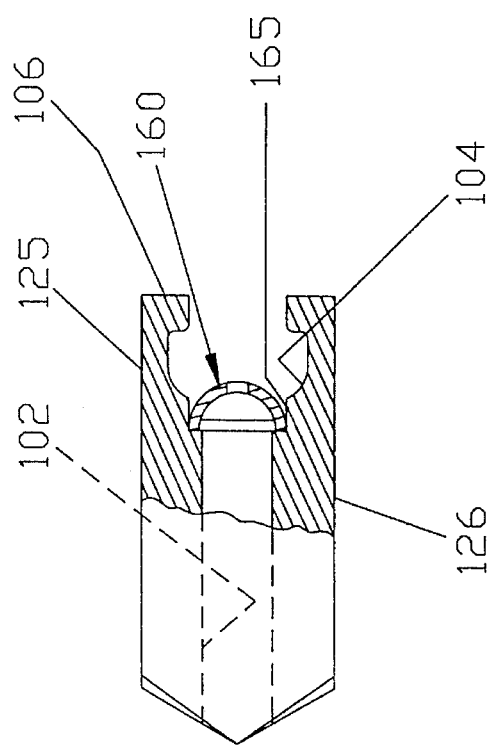
FIG. 2A is a side view similar to FIG. 2, but showing the provision of a tightening element to help hold drill bit 100 on drill shaft 200.
Figure 2:
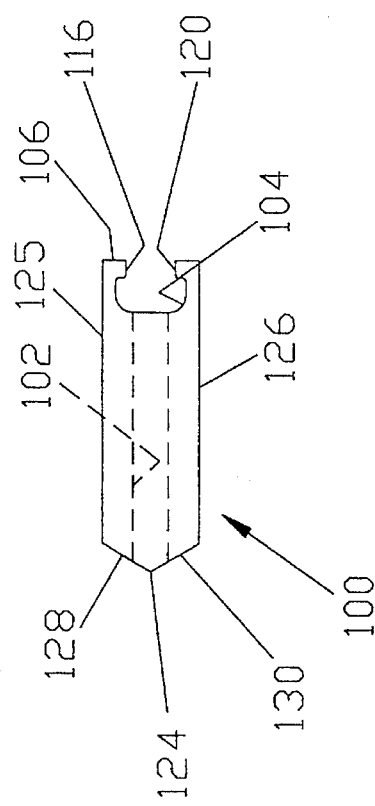
FIG. 2 is an enlarged side view of the drill bit shown in FIG. 1.
Figure 4A:
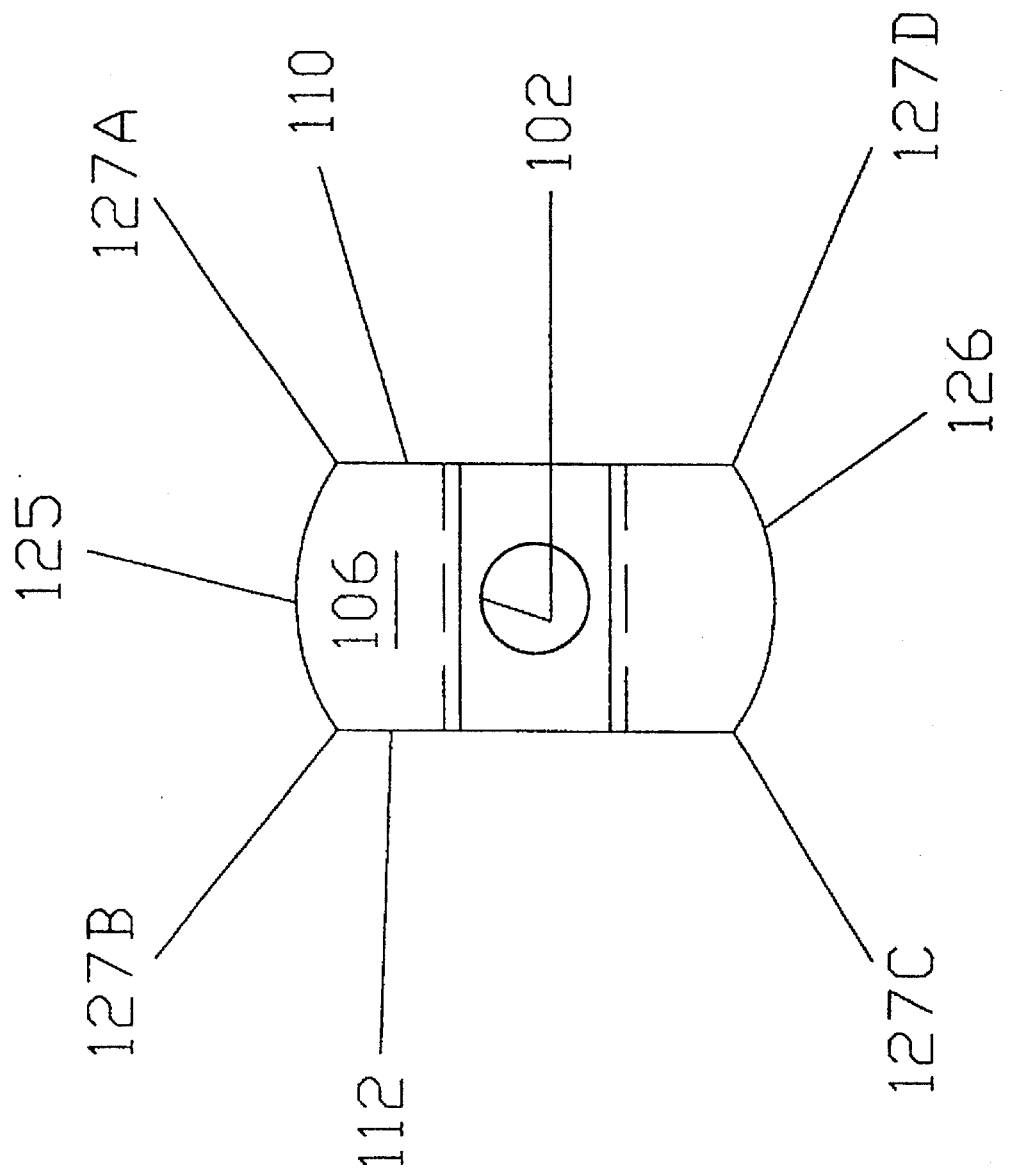
FIG. 4A is a rear view similar to FIG. 4, but showing a somewhat rectangular rear end 106.
Figure 6A:
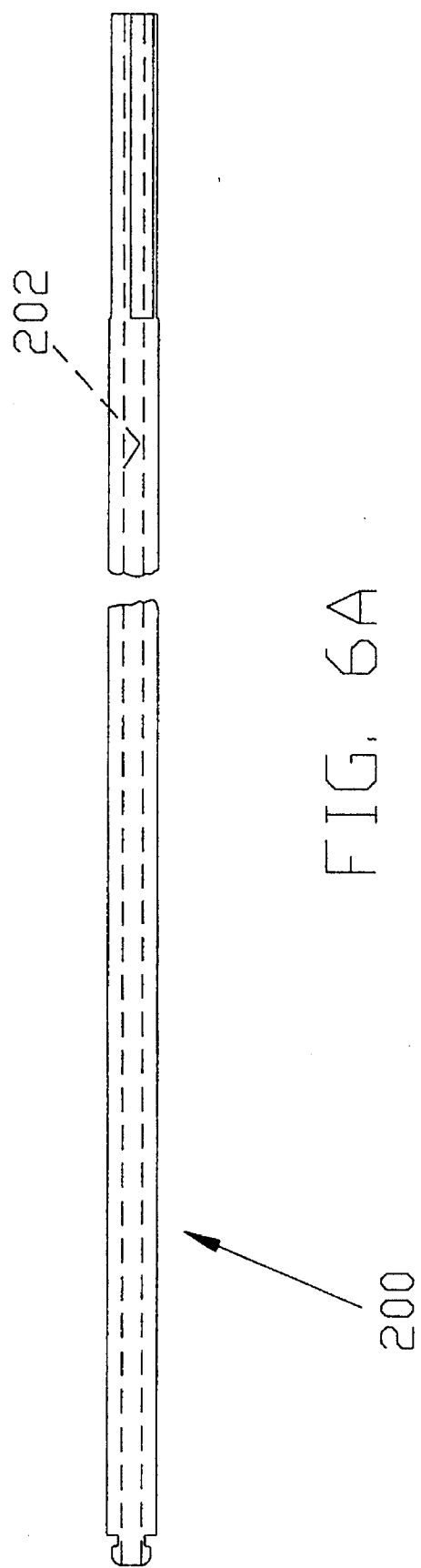
FIG. 6A is a side view similar to FIG. 6, but showing a dual diameter bore 202 extending the length of the shaft.

The details of the drill bit construction are more clearly shown in FIGS. 2, 3, 4 and 5. One portion of the tongue-and-groove interconnection 300 is provided in the drill bit 100 by forming a "D" shaped groove 104 (see FIG. 2) at the rear end 106 of the drill bit. The rear end 106 may be formed circular in shape for relatively small drill bits (see FIGS. 2–5), or it may be formed somewhat rectangular in shape (with fully radiused surfaces 125 and 126, as will hereinafter be discussed in further detail) for relatively large drill bits (see FIG. 4A). In either case, groove 104 passes completely through rear end 106, extending from one side 110 to the other side 112 (see FIG. 5) of the drill bit 100. This construction results in creating opposed depending locking ribs 116 and 120 (FIG. 2).

Drill bit 100 has a spade type configuration. As seen in FIG. 5, the sides 110 and 112 are sloped towards one another in the direction extending from the rear end 106 of the drill bit towards the forward end 124 (FIGS. 2 and 5). The specific angle of these sides to the center line of the drill bit is not critical. The angles are chosen such as to enable the drill to be turned smoothly into bone and to allow bone chips to flow away from the drill tip. At the same time, the drill bit's two other surfaces 125 and 126 are curved surfaces which lie along a constant radius projected from the longitudinal axis of the drill bit. In other words, curved surfaces 125 and 126 are full radiused projections from the longitudinal axis of the drill bit (see FIGS. 3, 4 and 4A). Surfaces 110, 112, 125 and 126 meet at corner edges 127A, 127B, 127C and 127D (see FIGS. 3 and 4A).

The configuration of the front end 124 of the drill bit is shown more clearly in FIGS. 2 and 3, when considered along with FIG. 5. The front end 124 is formed by two surfaces 128 and 130 which slope towards one another and meet at their apex. The bore 102 extends through the front end 124 to open on surfaces 128 and 130, thereby creating a concave rim 131 (see FIG. 5) bounded by apex edges 132 and 133 (see FIG. 3). Surfaces 128 and 130 are each formed with a relief angle, so that surface 128 slopes off from left to right, and surface 130 slopes off from right to left, when viewed from the point of reference of FIG. 3. Side edges 134 and 135 form the cutting edges for cutting into bone when the drill bit is rotated counterclockwise, when viewed from the point of reference of FIG. 3.

The other part of the tongue-and-groove interconnection 300 is formed at the front end of the rigid shaft 200 (see FIGS. 6 and 7). The front end of the drill shaft is in the form of a "D" shaped tongue 204 (see FIG. 6) of lesser diameter 206 than the diameter of the shaft 200. Tongue 204 is complementary in shape to the "D" shaped groove 104 in the drill bit 100. Tongue 204 is slightly forward of the main body of shaft 200 in order to form the locking slots 208 and 210. This construction enables the drill bit 100 to be locked to the rigid drill shaft 200 when the groove 104 is passed over the tongue 204 and the locking ribs 116 and 120 are placed into the locking slots 208 and 210, respectively.

If desired, and looking now at FIG. 2A, a tightening element 160 (such as a curved or conical spring washer) may be provided to help hold drill bit 100 on shaft 200. In such a case, drill bit 100 includes a counterbore 165 that is coaxial with bore 102. Tightening element 160 is seated in, and normally projects out of, counterbore 165 so as to be capable of yieldably projecting into groove 104. As a result of this construction, when groove 104 passes over tongue 204, tightening element 160 engages tongue 204 and thereby helps retain drill bit 100 on shaft 200.

Figure 7A:
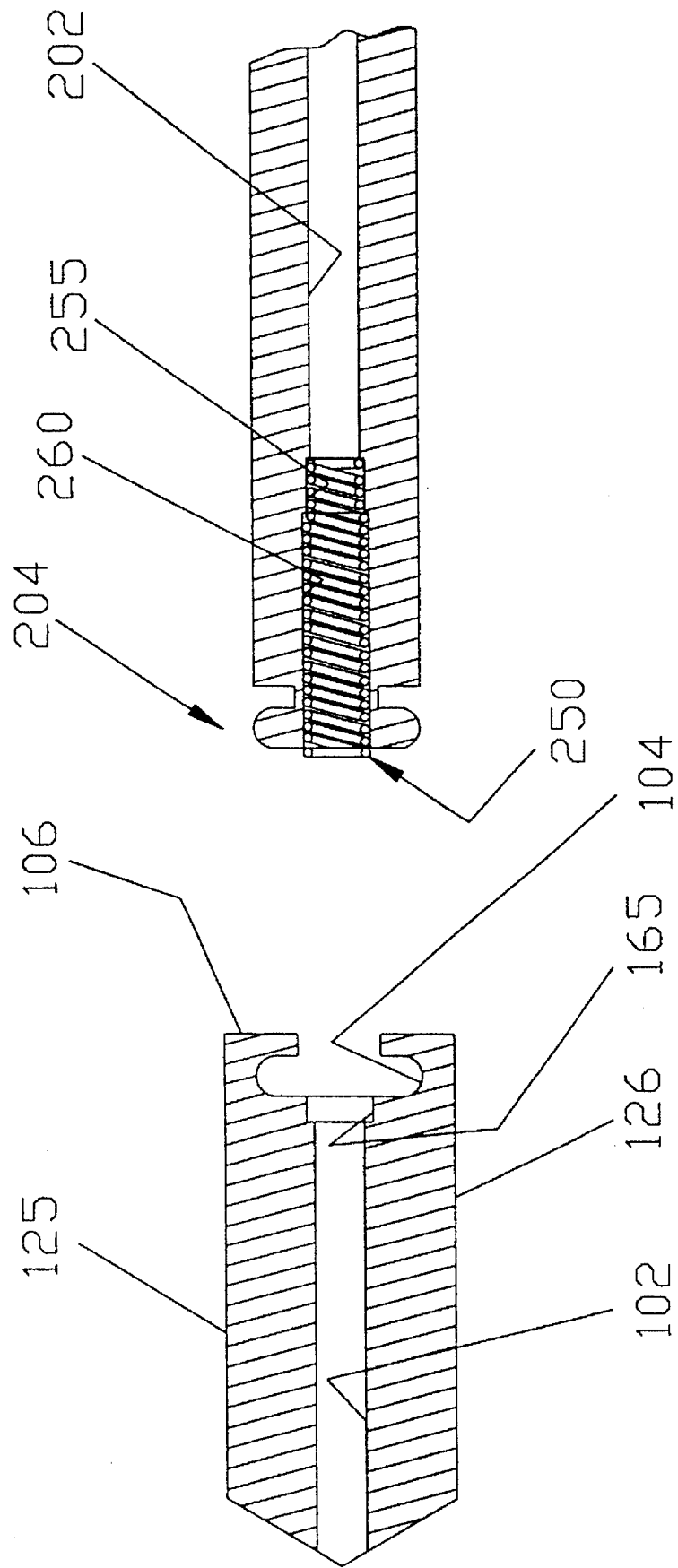
FIG. 7A is an exploded side view of another form of the modular drill of the present invention, showing the provision of a tightening element on the rigid drill shaft to help hold drill bit 100 on drill shaft 200.

Alternatively, and looking now at FIG. 7A, a tightening element 250 (such as an ordinary compression spring) may be provided on rigid drill shaft 200 to help hold drill bit 100 on the drill shaft. In this case, rigid drill shaft 200 includes a first counterbore 255 and a second counterbore 260. First counterbore 255 has a smaller diameter than second counterbore 260, and first counterbore 255, second counterbore 260 and tightening element 250 are sized so that the tightening element will make a binding fit with the walls of first bore 255, yet will yieldably project out of second counterbore 260. At the same time, tightening element 250 is hollow, with its internal diameter being greater than the diameter of the guidewire so that the guidewire can be accommodated therein. As a result of this construction, when groove 104 passes over tongue 204, tightening element 250 will engage drill bit 100 and then seat in the drill bit's counterbore 165 so as to help hold drill bit 100 on shaft 200.

The main body of shaft 200 is generally cylindrical in form, however, at its rear end 212 it is formed with a configuration which enables the shaft to be mounted into a chuck of a surgical drill. As shown in FIGS. 6 and 8, three flattened surfaces 214, 216 and 218 are formed at the rear end 212 and extend forward for a short distance from the shaft's rear end surface 219. For example, the surface 214 extends forward to and terminates at the shoulder 220 (see FIG. 6).

To employ the modular drill in a surgical procedure, the rear end 212 of shaft 200 is first tightened in a drill chuck (not shown). Then the drill bit 100 is assembled to the drill shaft 200 by positioning the drill bit's groove 104 adjacent to the shaft's tongue 204 and then sliding the bit sideways so that the locking ribs 116 and 120 are positioned within the locking slots 208 and 210, as indicated above, and the bores 102 and 202 are aligned.

Figure 10:
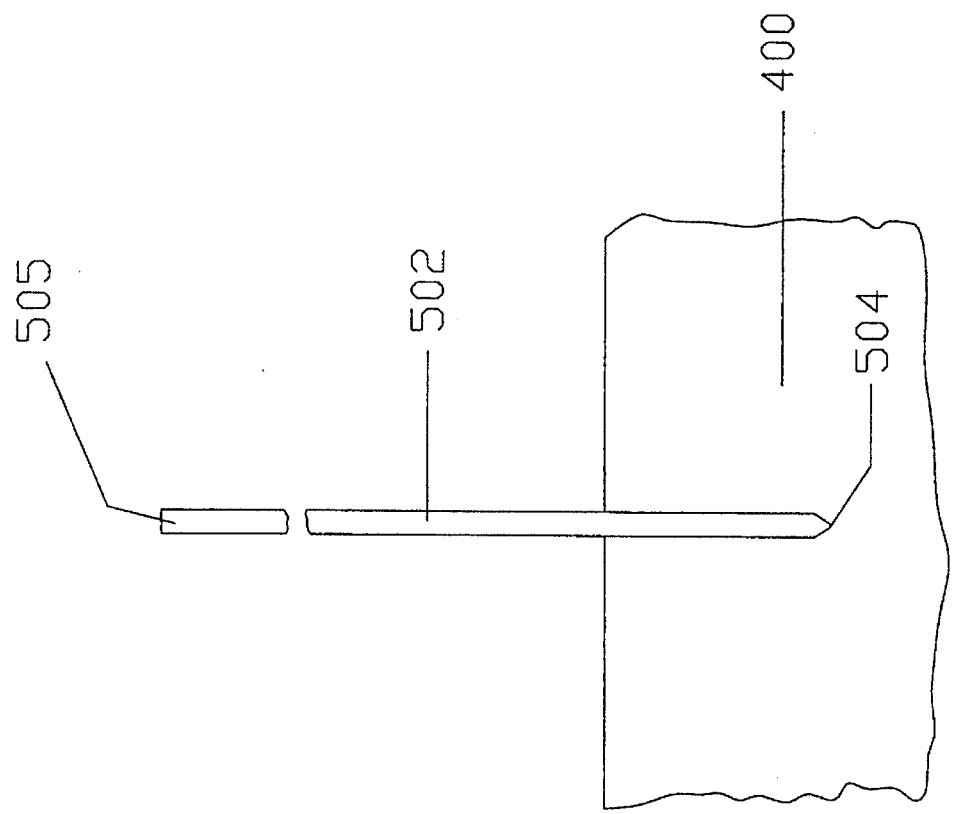
FIG. 10 is a side view of a guidewire that has been inserted into the same piece of bone.
Figure 9:
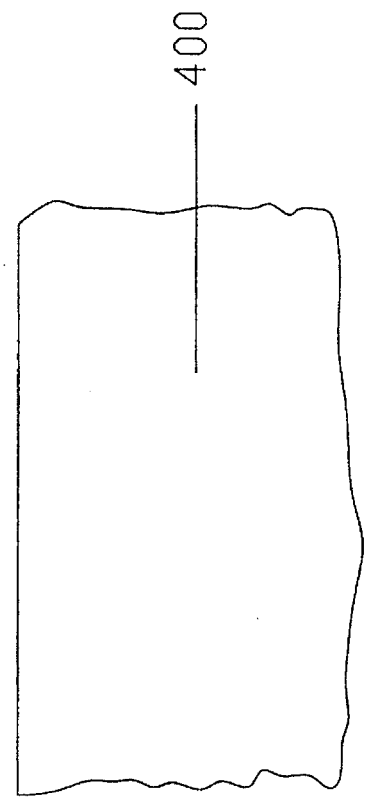
FIG. 9 is a side view of a piece of bone to which the method of the present invention may be applied to create a tunnel in the bone.
Figure 14:
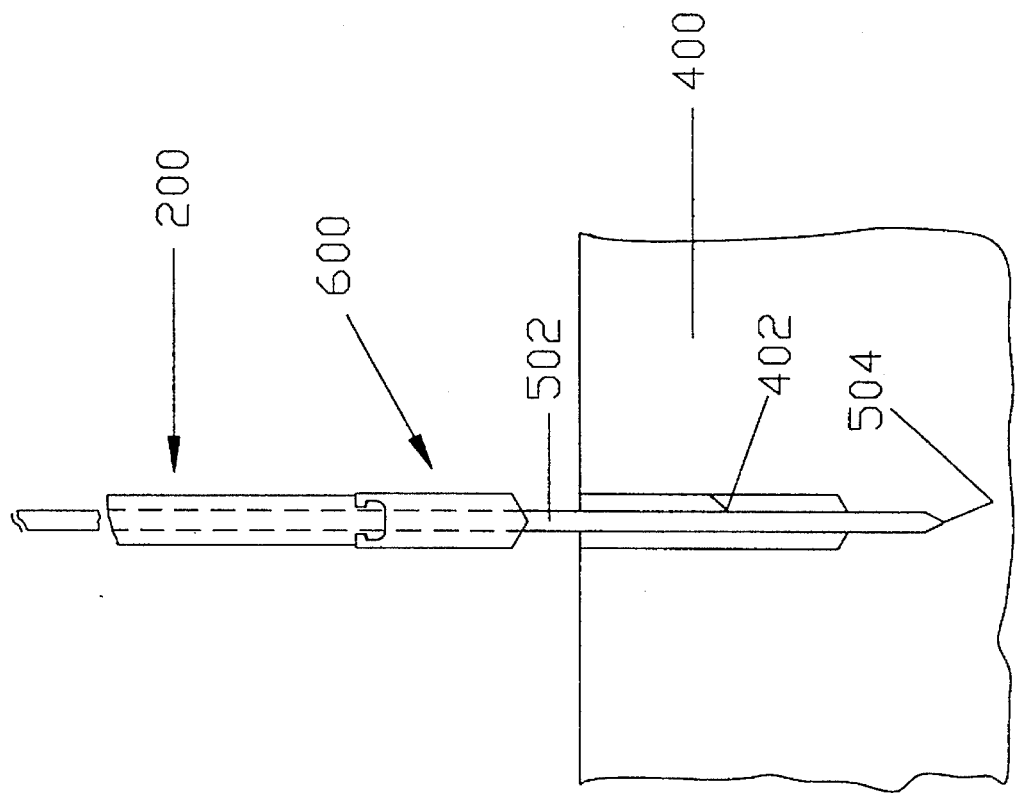
FIG. 14 is a side view of the same piece of bone showing the modular drill, having another drill bit of somewhat larger size, being introduced onto the guidewire.
Figure 13:
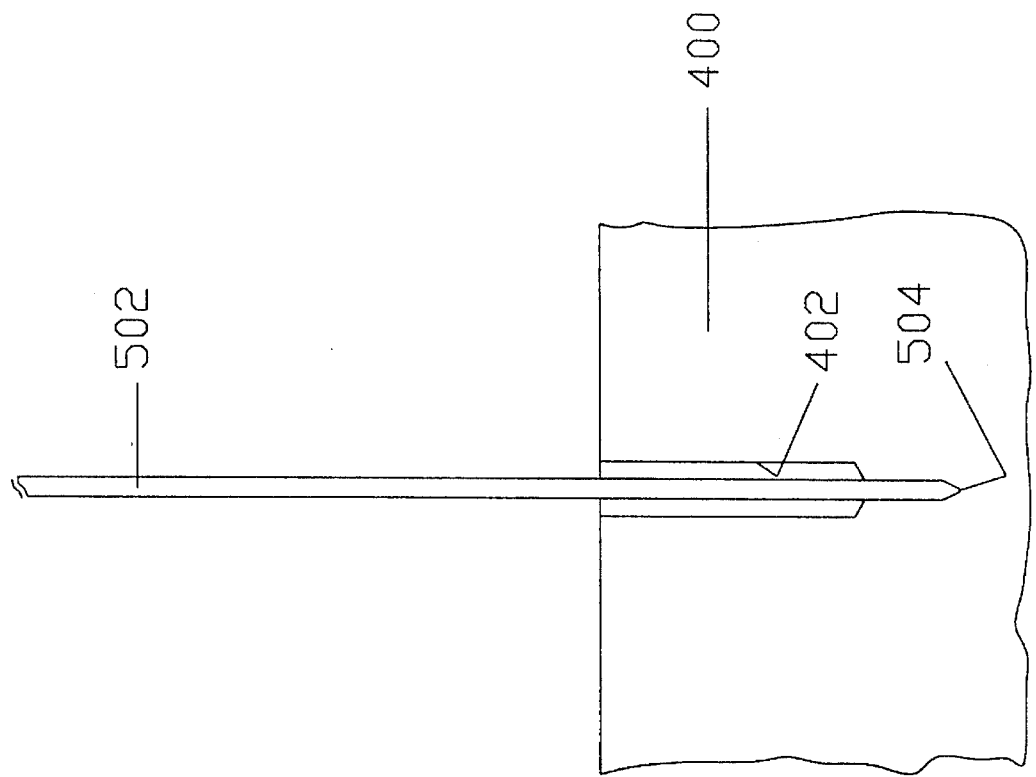
FIG. 13 is a side view of the same piece of bone after the modular drill shown in FIG. 12 has been withdrawn, with the guidewire still in place.
Figure 16:
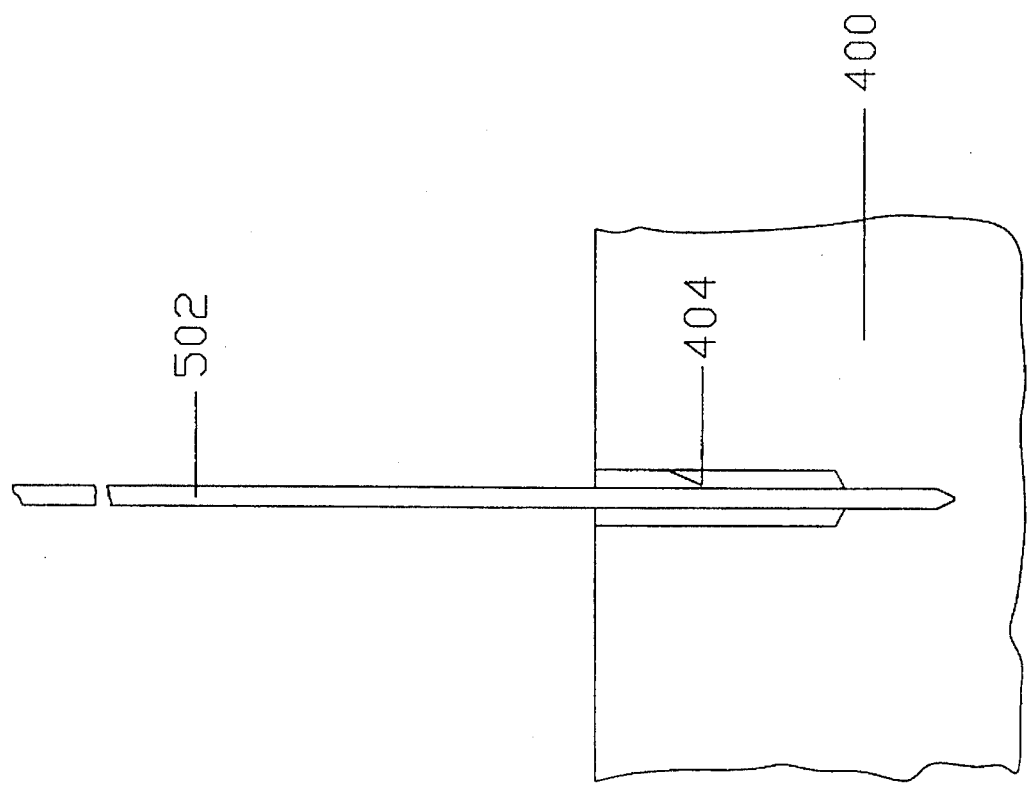
FIG. 16 is a side view of the same piece of bone, after the second modular drill assembly shown in FIG. 15 has been withdrawn, with the guidewire still in place.
Figure 15:
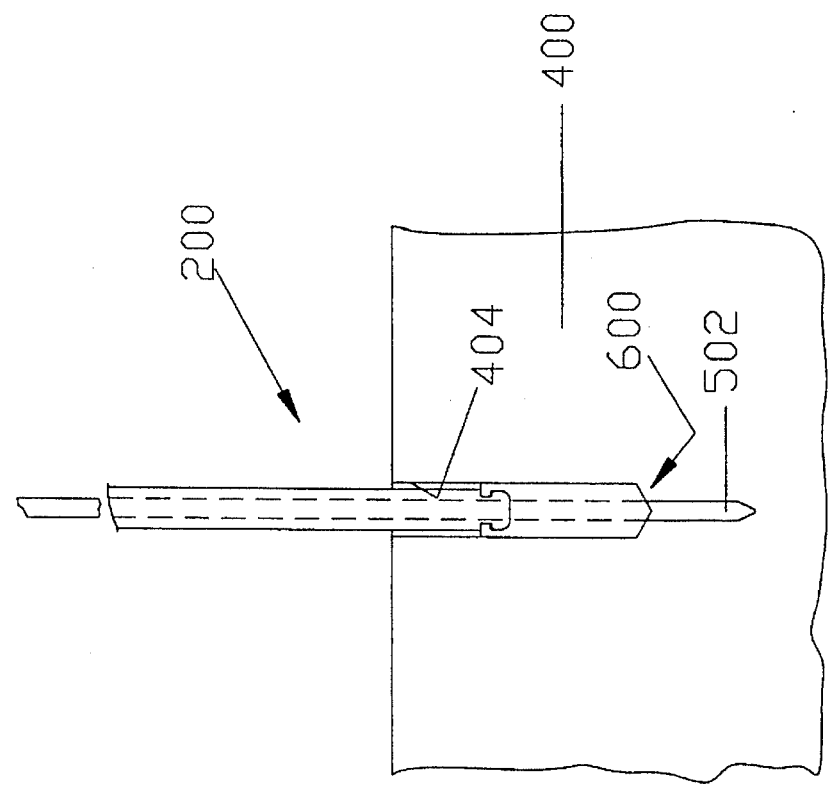
FIG. 15 is a side view of the same piece of bone, with the second modular drill assembly shown in FIG. 14 being advanced to cut into the bone to enlarge the previously created tunnel in the bone.
Figure 17:
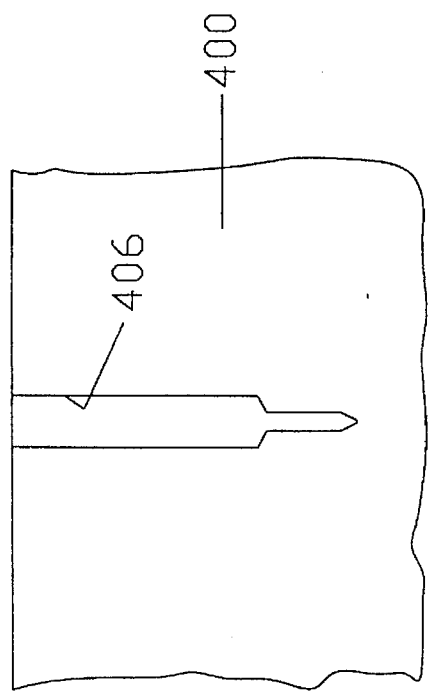
FIG. 17 is a side view of the same piece of bone after the guidewire has been removed.

Next, the thus assembled modular drill 4 may be employed to form a tunnel of desired diameter in bone, such as the piece of bone 400 shown in FIG. 9. The method involves the use of a guidewire 502 having a pointed end 504 and a free end 505. As indicated previously, this guidewire is preferably made of a surgically compatible material, e.g. stainless steel. The guidewire is first tapped or drilled into the bone 400 to a desired depth as shown in FIG. 10. Thereafter, a preassembled modular drill 4, chucked into a surgical drill (not shown), is moved down the guidewire (see FIG. 11) until it is in contact with the bone 400. The drill is then advanced along the guidewire into the bone (as shown in FIG. 12) so as to create a hole to a desired depth. After reaching such desired depth the modular drill is removed, thus leaving a hole 402 (FIG. 13) having the shape and dimensions of the drill bit that was employed to form the hole.

Where it is desired to provide an enlarged hole or tunnel in the bone, the guidewire 502 is allowed to remain in the bone 400, protruding therefrom as seen in FIG. 13. A larger sized drill bit 600 is then mounted on the same drill shaft 200. This can be done without removing shaft 200 from the surgical drill's chuck. The newly assembled modular drill is then passed down the guidewire 502 until it is in contact with the bone mass 400. The modular drill is then advanced down the guidewire (FIG. 15) in order to form the larger diameter bore or tunnel 404. The drilling implement is then removed from the bone and the larger diameter tunnel 404, with the guidewire 502 still protruding from the bone as seen in FIG. 16. Where still larger diameter holes are desired, this process can be repeated with still larger sized drill bits. Finally, when the desired diameter tunnel 406 has been created in the bone 400, the guidewire is removed (see FIG. 17).

Figure 19:
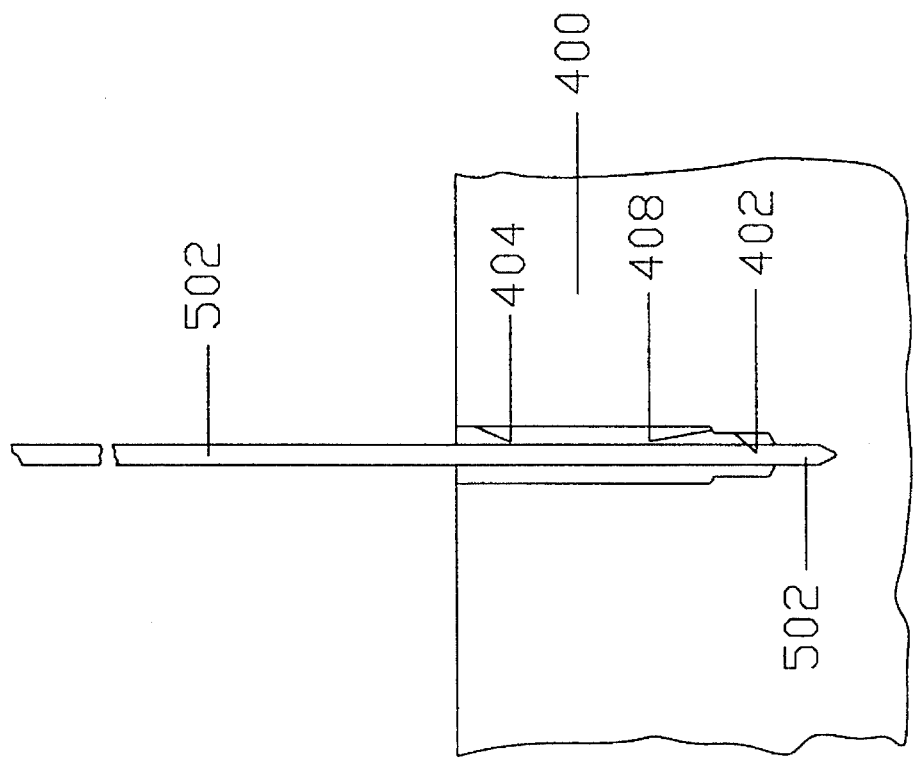
FIG. 19 is a side view of the same piece of bone after the second modular drill assembly shown in FIG. 18 has been withdrawn, with the guidewire still in place.
Figure 18:
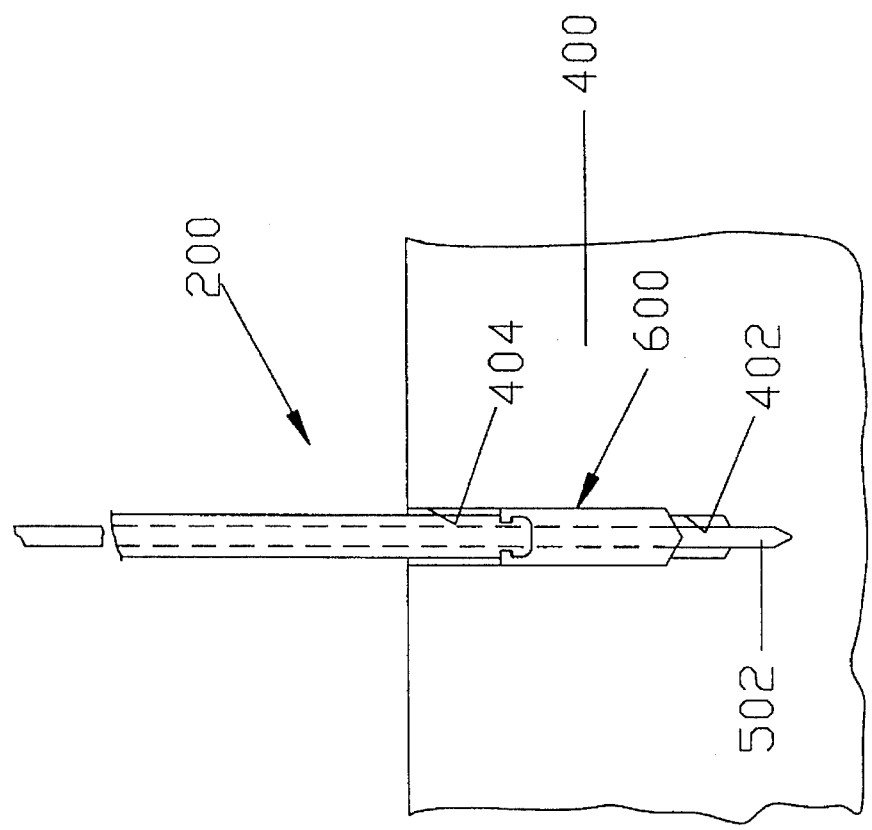
FIG. 18 is a view like that of FIG. 15, except that the second modular drill assembly, having a drill bit of somewhat larger size than the first modular drill assembly, has stopped at a shallower depth than the first modular drill assembly previously passed down the same guidewire.

The same procedure may be used to drill a stepped bone tunnel, where the larger diameter hole 404 is drilled to a shallower depth than the initial diameter hole 402, thereby leaving an annular shoulder 408 at the base of the larger diameter hole 404 (see FIGS. 18 and 19).

The entire drilling procedure employs a guidewire 502 which has a diameter of such dimension as to create a close sliding fit in the aligned bores 102 and 202 of the modular drill. Such an arrangement keeps the drill bit and shaft from moving relative to one another because of the mounting on the guidewire, while still enabling rotation of the modular drill on the guidewire to effect drilling into the bone. Further, the retention of the guidewire in the bone 400 during all drilling ensures that the hole or tunnel that is produced is on the same center line regardless of the number of drilling steps that are performed. This alignment is maintained even though successive drilling operations are applied to the bone, using different drill bits, since the modular drill assembly always moves down the same, fixed guidewire.

In order to facilitate drilling to a desired depth, rigid drill shaft 200 may have graduated markings 506 (see FIGS. 6 and 20) along its length to indicate the position of the drill bit tip relative to the outer surface of the bone.

The foregoing constitute only some of the possible forms of the present invention, which comprises a novel modular drill and a method of its use in forming tunnels into bone wherein the drill shaft need be mounted only once in the chuck of a drill, and the drill bits may be easily interchanged during the surgical procedure without having to dismount the shaft from the drill. It is also to be appreciated, of course, that various changes may be made in the configuration of the drill bit and/or the drill shaft, the materials of which they are made and the manner in which they are used, all without departing from the spirit and scope of the present invention.

Figure 20:
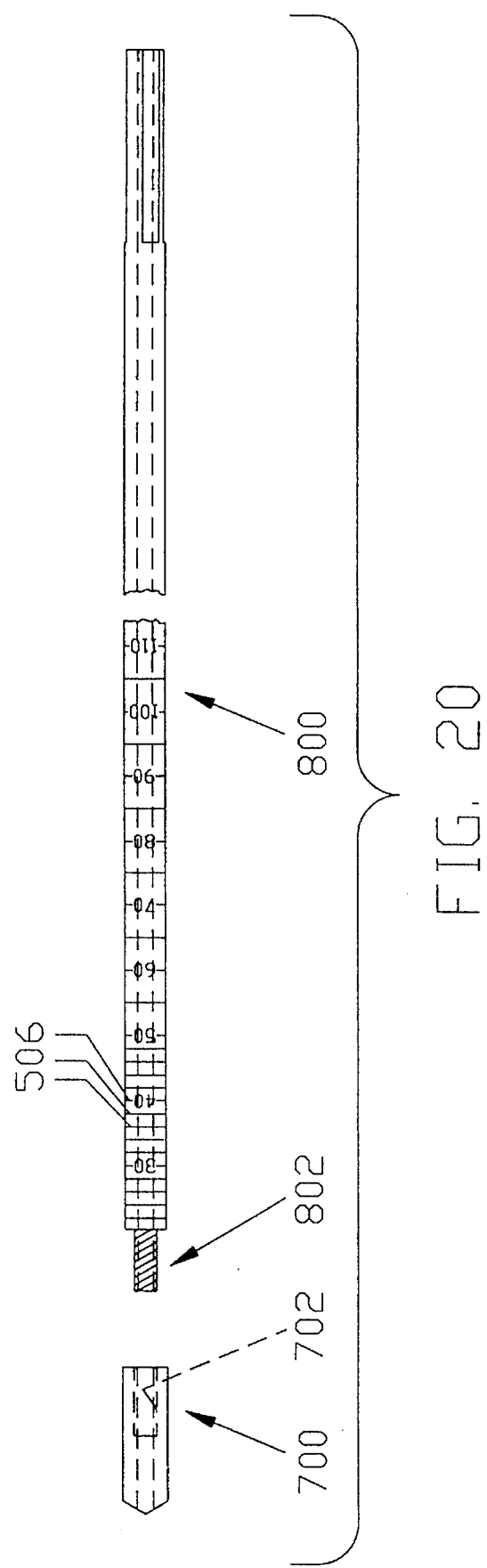
FIG. 20 is an exploded side view of another form of modular drill of the present invention, showing a different form of connection of the drill bit and drill shaft.

Thus, for example, while in the preferred embodiment of FIGS. 1–8, a tongue-and-groove interconnection is employed between the drill bit and drill shaft, a threaded connection may also be used. Such an arrangement is shown in FIG. 20, wherein a drill bit 700 having a threaded bore 702 is provided, along with a drill shaft 800 having a reduced threaded forward end 802. In this modification, the drill bit 700 is threaded onto the drill shaft 800. Standard threads or special thread forms may be used.

Alternatively, other known attachment means may be used to attach the drill bit to the drill shaft. By way of example, a dovetail mount or a bayonet mount may also be used.

Figure 20A:
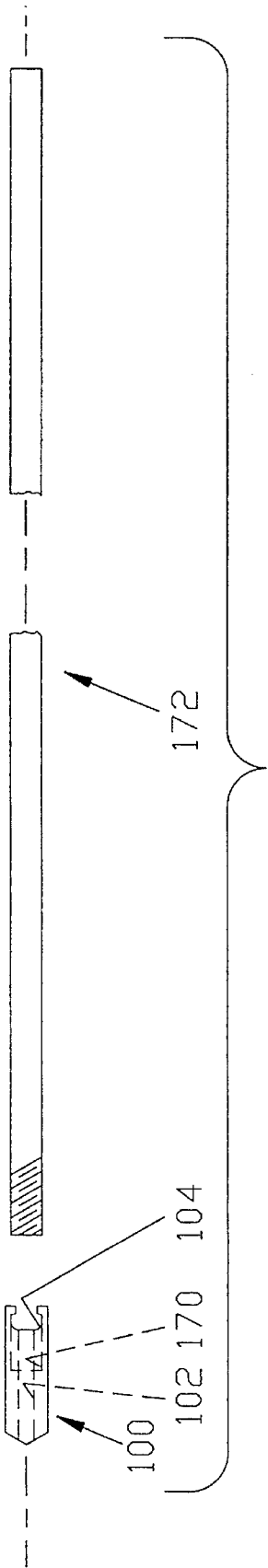
FIG. 20A is a an exploded side view showing a drill bit and retrieval means for retrieving the drill bit from the body in the event that it separates from the drill shaft during surgery.

In a further embodiment of the invention, the drill bit may be provided with retrieval means for retrieving the drill bit from the body in the event that it separates from the drill shaft during surgery. Thus, for example, and looking now at FIG. 20A, a threaded portion 170 is tapped into bore 102 to a specific depth. In the event that the drill bit becomes disengaged from the drill shaft during surgery, it can be retrieved by means of a threaded retrieval tool 172, also shown in FIG. 20A. During retrieval, the tool 172 is screwed into threaded portion 170, thereby allowing tool 172 to capture the drill bit for subsequent removal.

Figure 20B:
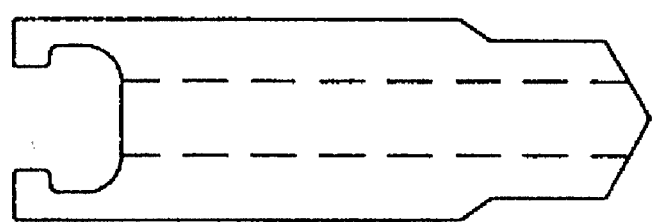
FIG. 20B is a side view of a stepped profile drill bit also formed in accordance with the present invention.

Also, although a drill bit having only one cutting profile has been shown and described above, it is also possible to form the drill bit with a plurality of cutting profiles, including a profile which includes more than one diameter. Thus, for example, and looking now at FIG. 20B, a two diameter spade type bit 175 is shown. Drill bit 175 may be employed to provide a stepped hole with a single pass of the modular drill. Alternatively, an exiting hole may be widened along some or all of its length by placing the stepped profile drill bit 175 into the exiting hole and drilling.

Although the modular drill has been generally described in the context of FIGS. 9–19 as being used to establish and progressively widen a bone tunnel, it could be used to drill a plurality of different holes in bone of varying size during a given surgical procedure. In either case there is the advantage of not having to re-chuck the drill in the surgical drilling implement each time a different size hole or larger diameter hole is to be drilled. It is only necessary to interchange the drill bit on the drill shaft.

Figure 22:
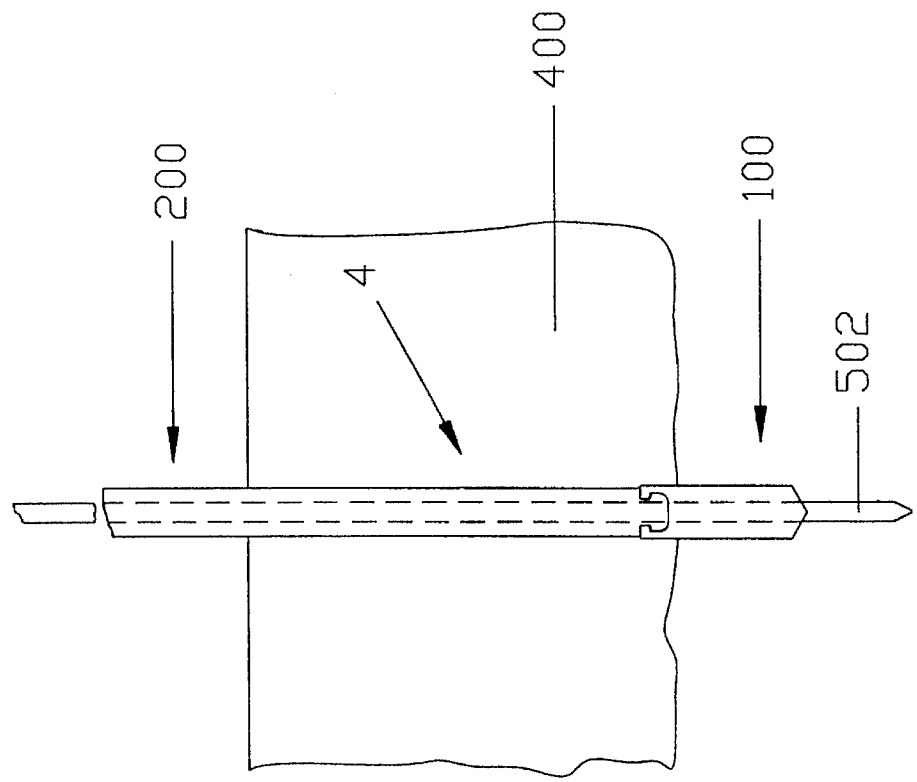
FIG. 22 is a view like that of FIG. 21, except that the modular drill is shown exiting the far side of bone 400.
Figure 21:
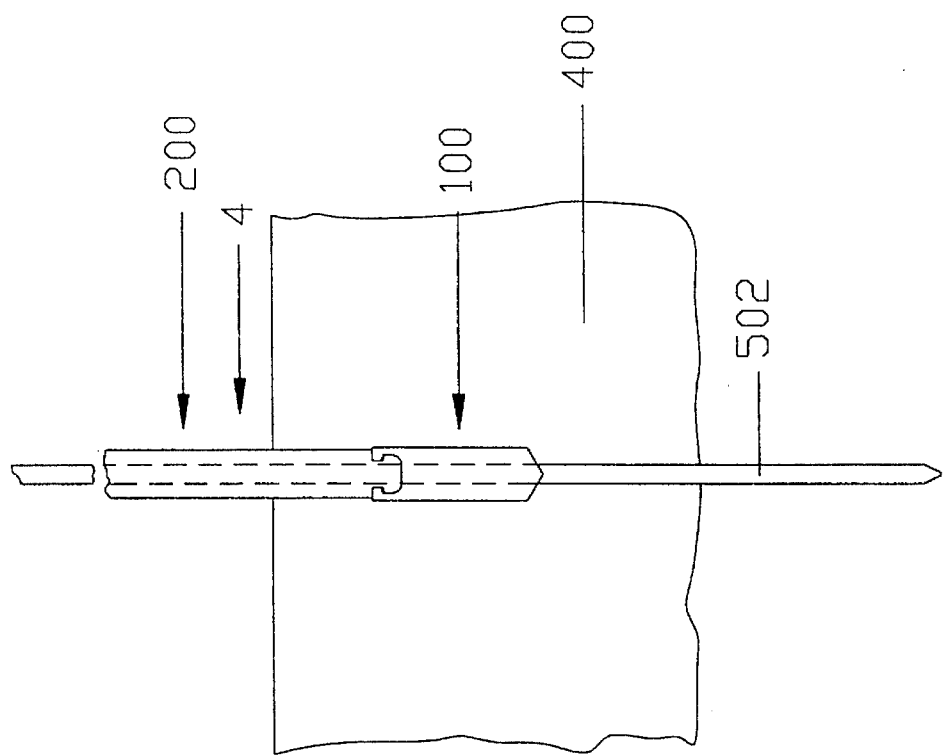
FIG. 21 is a view like that of FIG. 12, except that the guidewire extends completely through bone 400.

Additionally, although what has been described is the creation of one or more tunnels in bone that are "dead-ended", the modular drill could be used to drill all the way through the bone. See, for example, FIGS. 21 and 22, which are similar to the foregoing FIGS. 11 and 12, except that they show the guidewire 502 and drill 4 passing completely through bone 4.

Figure 23:
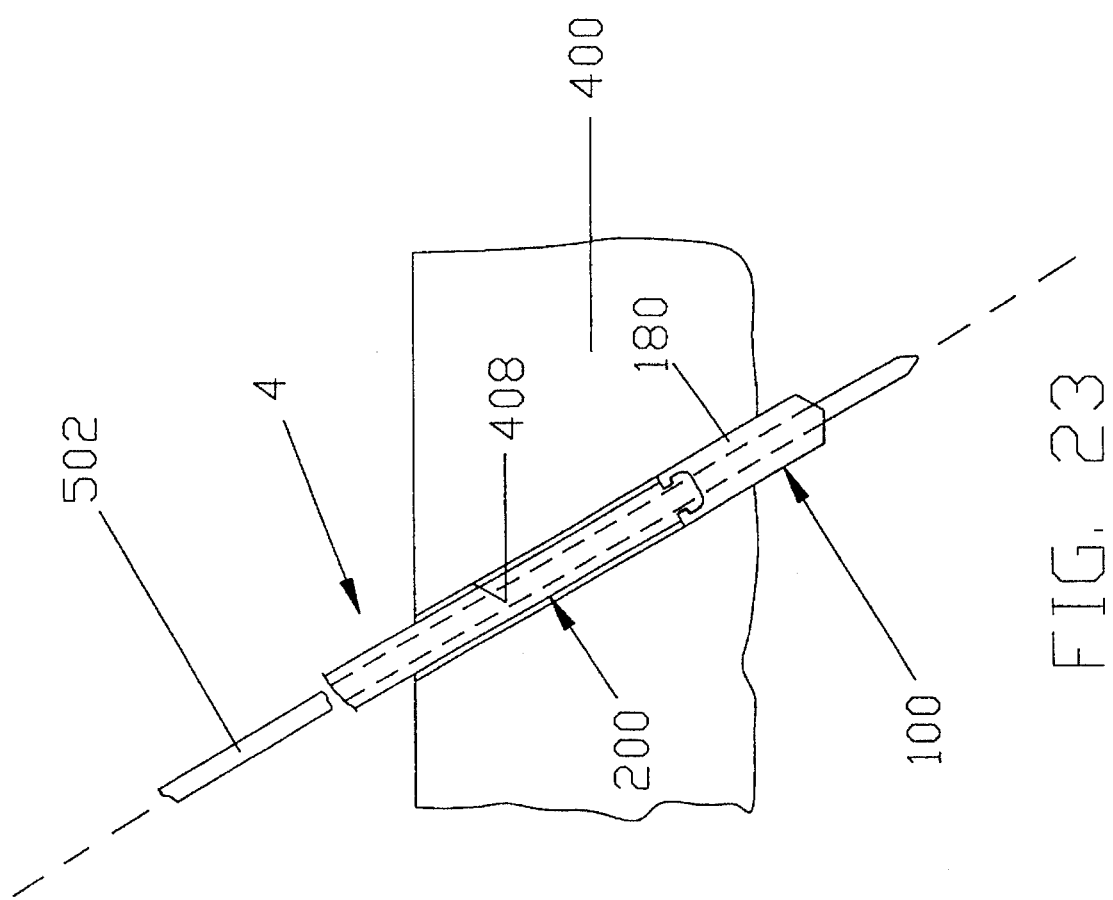
FIG. 23 is a side view of a piece of bone, showing a modular drill passing through the bone at an acute angle.

Furthermore, FIGS. 9–19, 21 and 22 show the use of the modular drill to create a tunnel in bone that is perpendicular to the outer surface of the bone. However, a hole may also be drilled at an angle to the vertical. FIG. 23 depicts drilling a through hole in a bone 400, at an angle to the vertical. The modular drill 4 is used to create the tunnel 408 in the manner described above. However, even though the guidewire 502 is deployed to align the drill, when the drill bit 100 drills through the other side of the bone, the guidewire becomes dislodged. It is possible, when this occurs, for the drill bit to migrate off-axis and/or to cause the exit portion of the tunnel to be widened, or become non-circular, or otherwise be deformed so that the tunnel is not of constant diameter throughout its length. This could seriously impair the surgical procedure. To avoid such a result it is important that the length of the drill bit be greater than its diameter, and that the drill bit be of relatively constant diameter. In practice, it has been found that where the length of the drill bit is at least twice its maximum diameter, a stable exit from the bone hole will be attained for a variety of angles. This result is illustrated in FIG. 23, which shows the drill bit 100 advanced through the bone, with the rear portion 180 of the drill bit still serving to guide and steady the modular drill to ensure that a linear tunnel 408 is created.

These and other changes of their type are all considered to be within the spirit and scope of the present invention.

It is anticipated that the present invention will have particular application in surgical procedures for ligament reconstruction. More particularly, in U.S. Pat. Nos. 4,772,286 issued Sep. 20, 1988 to Goble et al.; 4,927,421 issued May 22, 1990 to Goble et al.; 4,997,433 issued Mar. 5, 1991 to Goble et al.; 5,147,362 issued Sept. 15, 1992 to Goble; and Re. 34,293 issued Jun. 22, 1993 to Goble et al., a variety of devices and methods are disclosed for attaching a ligament (or a ligament substitute) to bone, in order that a detached ligament may be reattached to bone or a damaged ligament completely replaced. In all of the methods disclosed in the foregoing patents, it is necessary to form a hole completely through the tibia and a hole at least part way (or all the way) through the femur, with the tibial and femoral holes being aligned with one another. Thus, for example, in FIGS. 24 and 25, a knee joint 700 is shown where a tibia 705 and a femur 710 come together. A posterior cruciate ligament (PCL) 715 is shown extending between tibia 705 and femur 710. In order to replace or reconstruct the anterior cruciate ligament (ACL) using one of the methods disclosed in one of the aforementioned patents, it is necessary to bend the knee joint into the desired position and then drill a hole 720 through tibia 705 and a hole 725 into femur 710. Depending on which one of the methods is to be used, hole 725 may extend only part way through femur 710 or all the way through femur 710. Regardless, it is necessary that the holes 720 and 725 be aligned with one another.

The present invention provides an excellent means of forming bone holes 720 and 725. More particularly, once the knee has been put into the desired position, a guidewire is passed through tibia 705 and into femur 710. Depending on the circumstances, the guidewire may or may not exit on the far side of femur 710. Then a drill formed in accordance with the present invention is passed all the way through tibia 705 and part way or all the way through femur 710. Thereafter, one or both of the holes 720 and 725 may be enlarged, either part way or all the way along their length, simply by placing a larger drill bit on the drill shaft and passing the drill back down the guidewire, in the manner previously disclosed. Of course, bone hole 720 and 725 may also be formed in separate and distinct drilling steps, with equally beneficial results.

Figure 24:
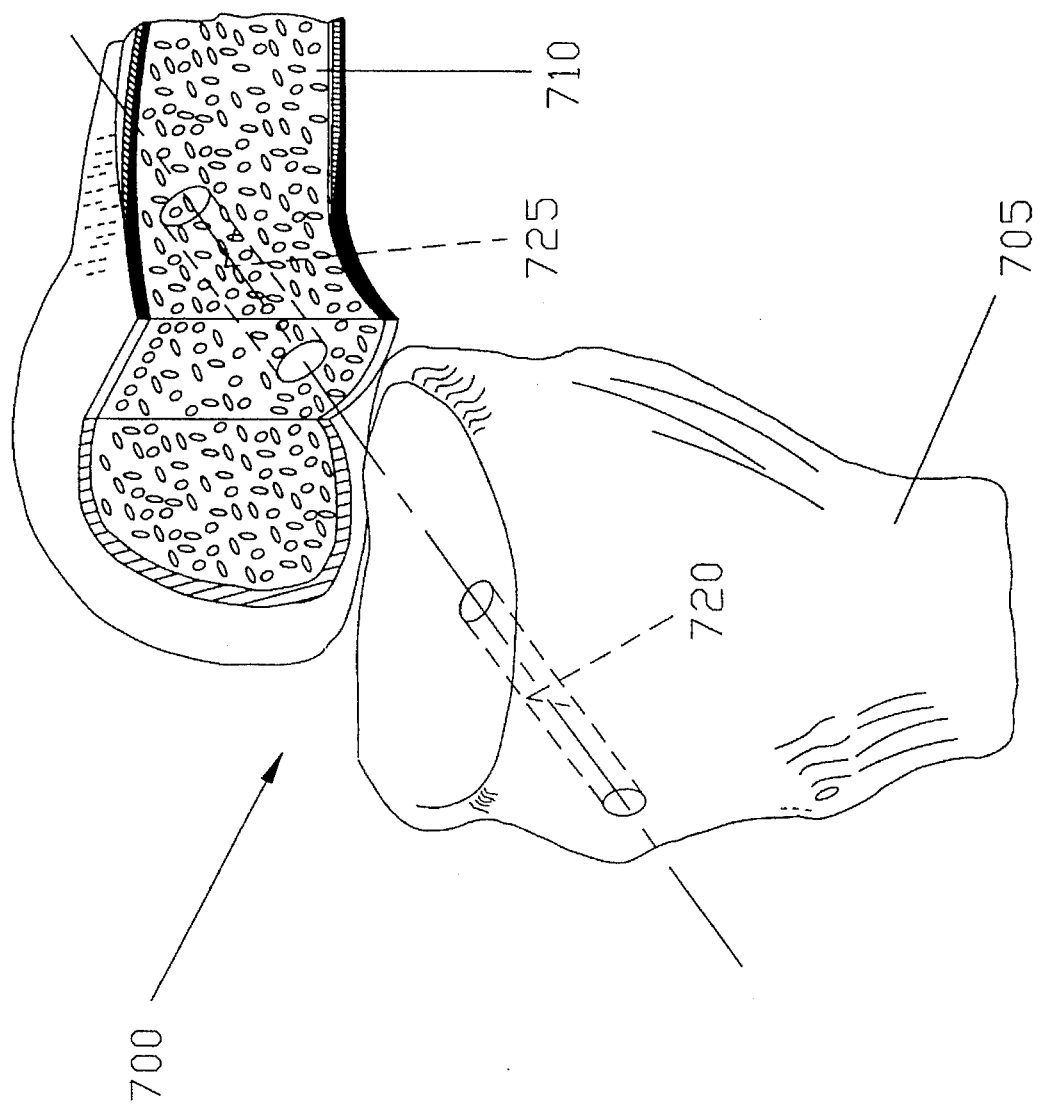
FIG. 24 is a side view of a knee joint, with bone tunnels extending in tibia 705 and femur 710.
Figure 25:
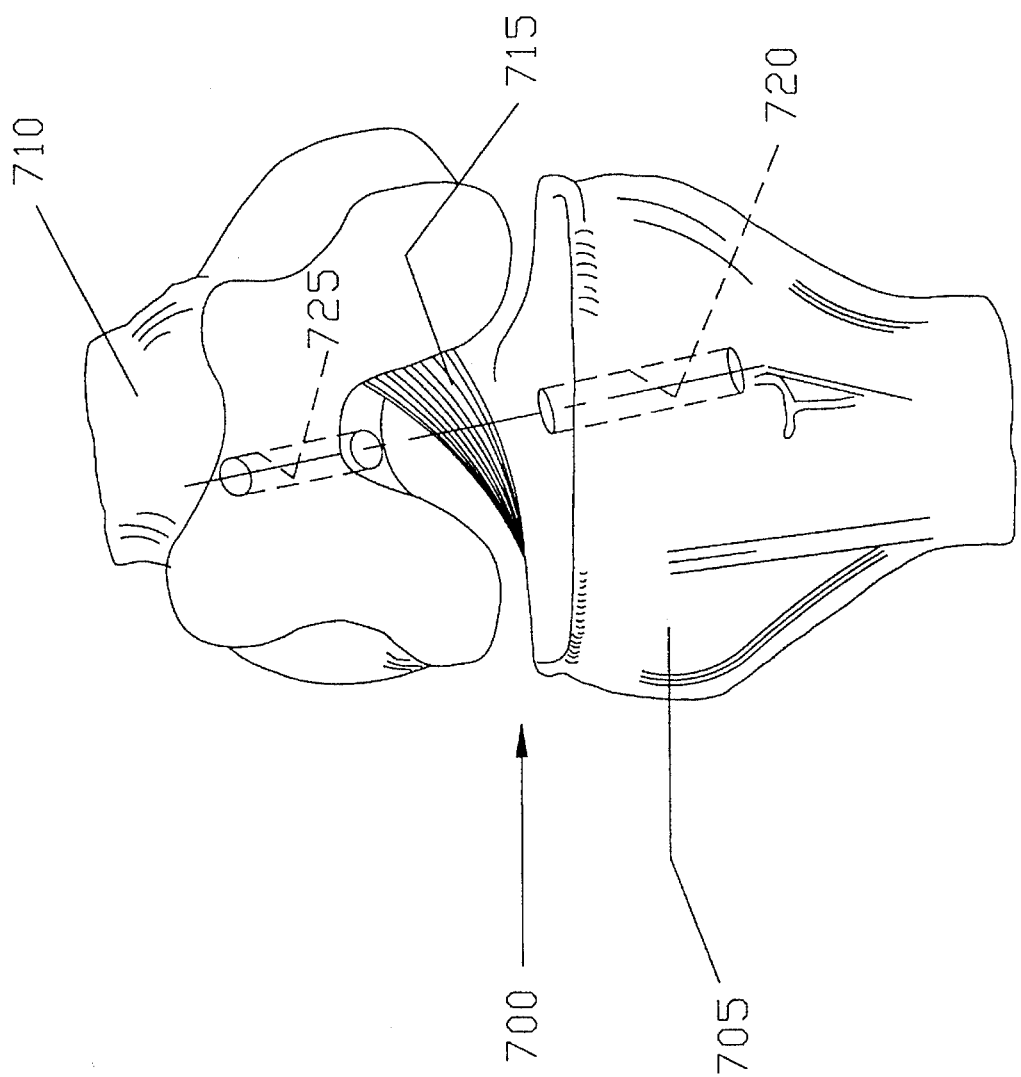
FIG. 25 is a front view of the same knee joint.

It will be appreciated that in an anterior cruciate ligament (ACL) reconstruction procedure such as that shown in FIGS. 24 and 25, it is important that the existing body structure not be inadvertently damaged during the hole-forming process. In particular, in the example of FIGS. 24 and 25, it is important that the posterior cruciate ligament (PCL) not be damaged by the drill as the holes 720 and 725 are formed. To this end, the drill bit's fully radiused surfaces 125 and 126 will avoid snagging or ripping or tearing the PCL if the drill bit should inadvertently contact the PCL during drilling.

Finally, in many surgical procedures the surgeon will need to pass a suture through a bone tunnel after the bone tunnel is formed. To this end, and looking now at FIG. 26, guidewire 502 may be provided with a side slotted eyelet 507 adjacent to its free end 505. A suture 508 is looped through the side slot 509 of eyelet 507 so that it will be captured by the eyelet. The suture may thereafter be drawn through one or more bone tunnels (e.g. the bone tunnels 720 and 725 shown in FIG. 26) by pulling the guidewire, pointed end 504 leading, through the one or more bone tunnels.

It is also to be appreciated that the modular drill of the present invention can be used to form holes in workpieces other than bone, in circumstances which may or may not relate to human and/or animal surgery. For example, the modular drill can be used to form a hole in a workpiece made of wood and/or plastic and/or metal, where the workpiece is entirely unrelated to human and/or animal surgery.

Still other uses for the novel apparatus and method of the present invention will be obvious to those skilled in the art.

What is claimed is:

1. A modular drill which is employed with a surgical drill tool for forming holes in bone, said modular drill comprising:

a drill bit having at least one cutting edge on one end thereof, and having a longitudinally extending bore passing through said drill bit;

a rigid drill shaft having mounting means at one end thereof for mounting said drill shaft on the surgical drill tool, and having a longitudinally extending bore passing through said drill shaft; and releasable interconnecting means formed on other ends of said drill shaft and said drill bit permitting assembly and disassembly of said drill bit to and from said drill shaft, said releasable interconnecting means being formed such that said bore passing through said drill bit is aligned with said bore passing through said drill shaft when said drill bit is assembled to said drill shaft, said releasable interconnecting means comprising a tongue-and-groove interconnection; said drill shaft comprising a central body portion, and a D-shaped tongue portion formed at said other end of said drill shaft and spaced slightly forward of said central body portion, wherein a pair of locking slots are formed in the space between said tongue portion and said central body portion of said drill shaft.

2. The modular drill of claim 1 wherein said other end of said drill bit is formed with a D-shaped groove.

3. The modular drill of claim 2 wherein said other end of said drill bit is provided with a pair of locking ribs extending into and adjacent to said D-shaped groove.

4. The modular drill of claim 1 wherein said drill bit further comprises a threaded counterbore adapted to be engaged by a threaded retrieval tool, whereby said drill bit may be captured by said retrieval tool when said drill bit is separated from said drill shaft.

5. A modular drill which is employed with a surgical drill tool for forming holes in bone, said modular drill comprising:

a drill bit having at least one cutting edge on one end thereof, and having a longitudinally extending bore passing through said drill bit;

a rigid drill shaft having mounting means at one end thereof for mounting said drill shaft on the surgical drill tool, and having a longitudinally extending bore passing through said drill shaft; and releasable interconnecting means formed on other ends of said drill bit and said drill shaft permitting assembly and disassembly of said drill bit to and from said drill shaft, said releasable interconnecting means being formed such that said bore passing through said drill bit is aligned with said bore passing through said drill shaft when said drill bit is assembled to said drill shaft;

wherein said releasable interconnecting means comprises a tongue-and-groove interconnecting means, a portion of which is located on said other ends of said drill bit and said drill shaft; and wherein a tongue portion is located on said other end of said rigid drill shaft, and a groove portion is located on said other end of said drill bit, and further wherein said groove portion comprises a counterbore, and spring means protruding therefrom, said spring means being adapted to engage said tongue portion when said drill bit and said drill shaft are assembled together.

6. A modular drill which is employed with a surgical drill tool for forming holes in bone, said modular drill comprising:

a drill bit having at least one cutting edge on one end thereof, and having a longitudinally extending bore passing through said drill bit;

a rigid drill shaft having mounting means at one end thereof for mounting said drill shaft on the surgical drill tool, and having a longitudinally extending bore passing through said drill shaft; and releasable interconnecting means formed on other ends of said drill bit and said drill shaft permitting assembly and disassembly of said drill bit to and from said drill shaft, said releasable interconnecting means being formed such that said bore passing through said drill bit is aligned with said bore passing through said drill shaft when said drill bit is assembled to said drill shaft;

wherein said releasable interconnecting means comprises a tongue-and-groove interconnecting means, a portion of which is located on said other ends of said drill bit and said drill shaft; and wherein a tongue portion is located on said other end of said rigid drill shaft, and a groove portion is located on the other end of said drill bit, and further wherein said tongue portion comprises a counterbore, and spring means protruding therefrom, said spring means being adapted to engage said groove portion when said drill bit and said drill shaft are assembled together.

7. The modular drill of claim 6 wherein said groove portion comprises a counterbore, said spring means being adapted to seat in said groove portion counterbore when said drill bit and said drill shaft are assembled together.

8. A modular drill which is employed with a surgical drill tool for forming holes in bone, said modular drill comprising:

a drill bit having at least one cutting edge on one end thereof, and having a longitudinally extending bore passing through said drill bit;

a rigid drill shaft having mounting means at one end thereof for mounting said drill shaft on the surgical drill tool, and having a longitudinally extending bore passing through said drill shaft; and releasable interconnecting means formed on other ends of said drill bit and said drill shaft permitting assembly and disassembly of said drill bit to and from said drill shaft, said releasable interconnecting means being formed such that said bore passing through said drill bit is aligned with said bore passing through said drill shaft when said drill bit is assembled to said drill shaft;

wherein said releasable interconnecting means comprises a tongue-and-groove interconnecting means, a portion of which is located on said other ends of said drill bit and said drill shaft; and wherein said drill bit further comprises a counterbore and spring means protruding therefrom, said spring means being adapted to engage said drill shaft when said drill bit and said drill shaft are assembled together.

9. A modular drill which is employed with a surgical drill tool for forming holes in bone, said modular drill comprising:

a drill bit having at least one cutting edge on one end thereof, and having a longitudinally extending bore passing through said drill bit;

a rigid drill shaft having mounting means at one end thereof for mounting said drill shaft on the surgical drill tool, and having a longitudinally extending bore passing through said drill shaft; and releasable interconnecting means formed on other ends of said drill bit and said drill shaft permitting assembly and disassembly of said drill bit to and from said drill shaft, said releasable interconnecting means being formed such that said bore passing through said drill bit is aligned with said bore passing through said drill shaft when said drill bit is assembled to said drill shaft;

wherein said releasable interconnecting means comprises a tongue-and-groove interconnecting means, a portion of which is located on said other ends of said drill bit and said drill shaft; and wherein said drill shaft further comprises a counterbore and spring means protruding therefrom, said spring means being adapted to engage said drill bit when said drill bit and said drill shaft are assembled together.

10. A modular drill assembly comprising:

a guidewire comprising a first end and a second end, said first end being pointed to facilitate releasably embedding said first end of said guidewire in bone; and a modular drill comprising:
  a drill bit having at least one cutting edge on one end thereof, and having a bore extending from one end to the other end of said drill bit;
  a drill shaft having mounting means at one end thereof for mounting said drill shaft to a surgical drill tool and having a bore extending from one end to the other end of said drill shaft;
  the respective bores sized with respect to the diameter of said guidewire so as to provide a close sliding fit therewith; and
  releasable interconnecting means formed in part on the other ends of said drill bit and said rigid drill shaft permitting assembly and disassembly of said drill bit to and from said drill shaft, said releasable interconnecting means comprising a tongue-and-groove interconnection and being formed such that said bore passing through said drill bit is aligned with said bore passing through said drill shaft when said drill bit is assembled to said drill shaft;

said drill shaft comprising a central body portion and a tongue portion formed at said other end of said drill shaft and spaced slightly forward of said central body portion, wherein a pair of locking slots are formed in the space between said tongue portion and said central body portion of said drill shaft; and whereby when said modular drill is mounted on said guidewire, said drill bit and said rigid drill shaft may not move relative to one another.

11. A modular drill which is employed with a surgical drill tool for forming holes in bone, said modular drill comprising:

a drill bit having at least one cutting edge on one end thereof, and having a longitudinally extending bore passing through said drill bit;

a rigid drill shaft having mounting means at one end thereof for mounting said drill shaft on the surgical drill tool, and having a longitudinally extending bore passing through said drill shaft; and releasable interconnecting means formed on other ends of said drill shaft and said drill bit permitting assembly and disassembly of said drill bit to and from said drill shaft, said releasable interconnecting means being formed such that said bore passing through said drill bit is aligned with said bore passing through said drill shaft when said drill bit is assembled to said drill shaft, said releasable interconnecting means comprising a tongue-and-groove interconnection; said drill shaft comprising a central body portion, and a tongue portion formed at said other end of said drill shaft and spaced slightly forward of said central body portion, wherein a pair of locking slots are formed in the space between said tongue portion and said central body portion of said drill shaft.

12. A modular drill assembly comprising:

a drill bit having a cutting edge at a first end thereof, and having a bore extending axially completely through said drill bit;

a drill shaft having mounting means at a first end thereof for mounting said drill shaft on a drill tool, and having a bore extending axially through said drill shaft; and releasable interconnecting means formed on second ends of said drill bit and said drill shaft permitting assembly and disassembly of said drill bit to and from said drill shaft, said interconnecting means being formed such that said bore extending through said drill bit is aligned with said bore extending through said drill shaft when said drill bit is assembled to said drill shaft;

wherein said releasable interconnecting means comprises a tongue-and-groove interconnection means disposed on said second ends of said drill bit and said drill shaft; and wherein a tongue portion is disposed on one of said second ends and a groove portion is disposed in the other of said second ends; and wherein said other of said second ends is provided with a counterbore, and spring means protrude from said counterbore to engage said tongue portion when said drill bit and said drill shaft are assembled together.

13. A modular drill assembly comprising:

a drill bit having a cutting edge at a first end thereof, and having a bore extending axially completely through said drill bit;

a drill shaft having mounting means at a first end thereof for mounting said drill shaft on a drill tool, and having a bore extending axially through said drill shaft; and releasable interconnecting means formed on second ends of said drill bit and said drill shaft permitting assembly and disassembly of said drill bit to and from said drill shaft, said interconnecting means being formed such that said bore extending through said drill bit is aligned with said bore extending through said drill shaft when said drill bit is assembled to said drill shaft;

wherein said releasable interconnecting means comprises a tongue-and-groove interconnection means disposed on said second ends of said drill bit and said drill shaft; and wherein a tongue portion is disposed on one of said second ends and a groove portion is disposed in the other of said second ends; and spring means protrude from said counterbore to engage said groove portion when said drill bit and said drill shaft are assembled together.

* * * * *